(12) United States Patent
Friesner et al.

(10) Patent No.: US 8,987,944 B2
(45) Date of Patent: Mar. 24, 2015

(54) ARRANGEMENT FOR CONTACTLESS POWER TRANSMISSION AND GROUNDING IN A COMPUTED TOMOGRAPHY SYSTEM

(75) Inventors: Horst Friesner, Altendorf (DE); Florian Hofmann, Erlangen (DE); Thomas Luthardt, Bamberg (DE); Helmut Repp, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 373 days.

(21) Appl. No.: 13/269,265

(22) Filed: Oct. 7, 2011

(65) Prior Publication Data

US 2012/0262001 A1    Oct. 18, 2012

(30) Foreign Application Priority Data

Oct. 7, 2010    (DE) .......................... 10 2010 042 124

(51) Int. Cl.
| | | |
|---|---|---|
| *H01F 38/00* | (2006.01) | |
| *A61B 6/03* | (2006.01) | |
| *A61B 6/00* | (2006.01) | |
| *H01P 1/06* | (2006.01) | |
| *H02J 5/00* | (2006.01) | |
| *H02J 17/00* | (2006.01) | |

(52) U.S. Cl.
CPC .............. *A61B 6/032* (2013.01); *A61B 6/4014* (2013.01); *A61B 6/56* (2013.01); *H01P 1/069* (2013.01); *H02J 5/005* (2013.01); *H02J 17/00* (2013.01)
USPC .......................................................... 307/104

(58) Field of Classification Search
USPC ................................ 307/104; 375/4, 15, 197
See application file for complete search history.

(56) References Cited

U.S. PATENT DOCUMENTS

| 4,109,631 | A | * | 8/1978 | Miyao ........................... 123/604 |
|---|---|---|---|---|
| 5,063,377 | A | * | 11/1991 | Smith ........................... 345/110 |
| 5,140,696 | A | | 8/1992 | Fox |
| 5,521,444 | A | * | 5/1996 | Foreman ....................... 307/104 |
| 6,608,569 | B2 | * | 8/2003 | Herold et al. ................. 340/999 |
| 7,197,113 | B1 | * | 3/2007 | Katcha et al. ................. 378/101 |
| 2011/0140429 | A1 | * | 6/2011 | Bohori et al. .................. 290/44 |

FOREIGN PATENT DOCUMENTS

| DE | 692 26 498 T2 | 4/1999 |
|---|---|---|
| DE | 103 56 109 A1 | 7/2005 |
| DE | 10 2008 044 647 A1 | 3/2009 |

OTHER PUBLICATIONS

German Office Action dated Jul. 21, 2011 for corresponding German Patent Application No. DE 10 2010 042 124.3 with English translation.

* cited by examiner

*Primary Examiner* — Rexford Barnie
*Assistant Examiner* — Daniel Kessie
(74) *Attorney, Agent, or Firm* — Lempia Summerfield Katz LLC

(57) ABSTRACT

The present embodiments include an arrangement for contactless transmission of electrical power between a fixed gantry section and a gantry section of a computed tomography system that is rotatable about an axis of rotation. The arrangement includes a first carrier ring in annular form arranged on the rotatable gantry section in an electrically conductive manner, and at least one first conductor element arranged in or on the first carrier ring, the at least one first conductor element being insulated from the first carrier ring and being for contactless receiving of the electrical power. The arrangement also includes at least one grounding slip ring arranged in or on the first carrier ring. The at least one grounding slip ring is connected to the first carrier ring in an electrically conductive manner.

16 Claims, 3 Drawing Sheets

18 Grounding Collector
17 Grounding Slip Ring
13 First Conductor Element
12 First Carrier Ring

ARRANGEMENT FOR CONTACTLESS POWER TRANSMISSION AND GROUNDING IN A COMPUTED TOMOGRAPHY SYSTEM This application claims the benefit of DE 10 2010 042 124.3, filed on Oct. 7, 2010.

BACKGROUND

The present embodiments relate to an arrangement for contactless transmission of power between a fixed gantry section and a gantry section of a computed tomography system rotatable about an axis of rotation.

In the case of computer tomographs, a contactless slip ring system is employed for data transmission (e.g., as known from U.S. Pat. No. 5,140,696 A). The data transmission system includes a transmitter unit on the rotating part and a receiver unit on the stationary part. The transmitter unit has at least one high frequency line connected to a transmitter as a transmit antenna. The transmitter is arranged on a periphery of the rotating part of the rotating frame. The receiver unit includes a receiver and at least one receive antenna connected to the receiver. The at least one receive antenna is formed by a short section of a high frequency line. Upon operation of the computer tomography, the transmit antenna moves past the receive antenna fixed to the stationary part at a slight distance therefrom, so that signals propagating on the transmitting high frequency line crosstalk in a near field on the receive antenna.

In addition to the data, electrical power for supplying power to electrical components is transmitted from the stationary part to the rotating part. DE 10 2008 044 647 A1 discloses a computed tomography device that is provided with a stationary part and a rotating part. The rotating part is embodied in a rotatable manner in relation to the stationary part. Electrical power is transmitted from the stationary part to an X-ray tube provided for the rotating part in a contactless manner. An electromagnetic induction transformer with a primary winding and a secondary winding is used. The primary winding in provided on the stationary part, and the secondary winding is provided on the rotating part.

The rotating part is to be grounded. The grounding of the stationary part is connected to the grounding of the rotating part. This is effected, for example, with grounding slip rings and brushes. The grounding is an electrically conductive connection to the electrical potential of the earth. The grounding is a form of ground connection. The ground connection, however, does not have to be the ground potential. Using ground connection, a conductive connection with the conductive environment is created. If this environment includes the earth or is connected to the earth in a conductive manner, a grounding exists.

SUMMARY AND DESCRIPTION

The present embodiments may obviate one or more of the drawbacks or limitations in the related art. For example, an improved arrangement for grounding two gantry sections of a computed tomography system that are rotatable relative to each other is provided.

The present embodiments include an arrangement for contactless transmission of electrical power between a fixed gantry section and a gantry section of a computed tomography system rotatable about an axis of rotation. The arrangement includes a first carrier ring arranged in annular form on the rotatable gantry section in an electrically conductive manner, and at least one first conductor element arranged in or on the first carrier ring. The at least one first conductor element is insulated from the first carrier ring and is configured for contactless receiving of the electrical power. In addition, the arrangement includes a grounding slip ring arranged in or on the first carrier ring. The grounding slip ring is connected to the first carrier ring in an electrically conductive manner. The present embodiments offer the advantage that as a result of the integration of the grounding system in the contactless first carrier ring, assembly effort may be saved. In addition, the grounding ring may be integrated in a space-saving manner.

In one embodiment, the arrangement may include a grounding collector that is arranged on a second carrier ring of the fixed gantry section.

The present embodiments also include an arrangement for contactless transmission of electrical power between a fixed gantry section and a gantry section of a computed tomography system rotatable about an axis of rotation. The arrangement includes a second carrier ring in annular form arranged on the fixed gantry section in an electrically conductive manner and at least one second conductor element arranged in or on the second carrier ring. The at least one second conductor element is insulated from the second carrier ring and is configured for contactless emission of the electrical power. The arrangement includes at least one grounding slip ring arranged in or on the second carrier ring. The at least one grounding slip ring is connected to the second carrier ring in an electrically conductive manner.

The present embodiments offer the advantage that as a result of the integration of the grounding system in the contactless first carrier ring, assembly effort may be saved. In addition, the grounding ring may be integrated in a space-saving manner.

In one embodiment, the arrangement may include a grounding collector that is arranged on a first carrier ring of the rotatable gantry section.

The at least one first or the at least one second conductor element may be embodied in annular form.

In one embodiment, the grounding slip ring may be embodied in annular form.

In another embodiment, the grounding collector may form an electrically conductive sliding contact with the grounding slip ring.

The present embodiments also include an arrangement for contactless transmission of electrical power between a fixed gantry section and a gantry section of a computed tomography system rotatable about an axis of rotation. The arrangement includes a first carrier ring arranged in annular form on the rotatable gantry section in an electrically conductive manner, and at least one first conductor element arranged in or on the first carrier ring. The at least one first conductor element is insulated from the first carrier ring and is configured for contactless receiving of the electrical power. The arrangement includes at least one grounding collector that is arranged on a second carrier ring of the fixed gantry section or the fixed gantry section. The at least one grounding collector forms an electrically conductive sliding contact with the first carrier ring or the rotatable gantry section. In order to slide on the rotatable gantry section, the at least one grounding collector is to be rendered usable using surface treatments such as tempering, galvanic plating or polishing. The present embodiments offer the advantage that as a result of an integration of the grounding system in the contactless first and second carrier ring, assembly effort may be saved.

The present embodiments also include an arrangement for contactless transmission of electrical power between a fixed gantry section and a gantry section of a computed tomography system rotatable about an axis of rotation. The arrangement includes a second carrier ring in annular form arranged on the fixed gantry section in an electrically conductive manner, and at least one second conductor element arranged in or on the second carrier ring. The at least one second conductor element is insulated from the second carrier ring and is configured for contactless emission of the electrical power. The arrangement also includes at least one grounding collector that is arranged on a first carrier ring of the rotatable gantry section or on the rotatable gantry section. The at least one grounding collector forms an electrically conductive sliding contact on the second carrier ring or the fixed gantry section. In order to slide on the rotatable gantry section, the at least one grounding collector is to be rendered usable using surface treatments such as tempering, galvanic plating or polishing. The present embodiments offer the advantage that using an integration of the grounding system in the contactless first and second carrier ring, assembly effort may be saved.

The present embodiments also include a computed tomography system with a gantry with two gantry sections and one embodiment of an arrangement.

DETAILED DESCRIPTION OF THE DRAWINGS

Figure 1:
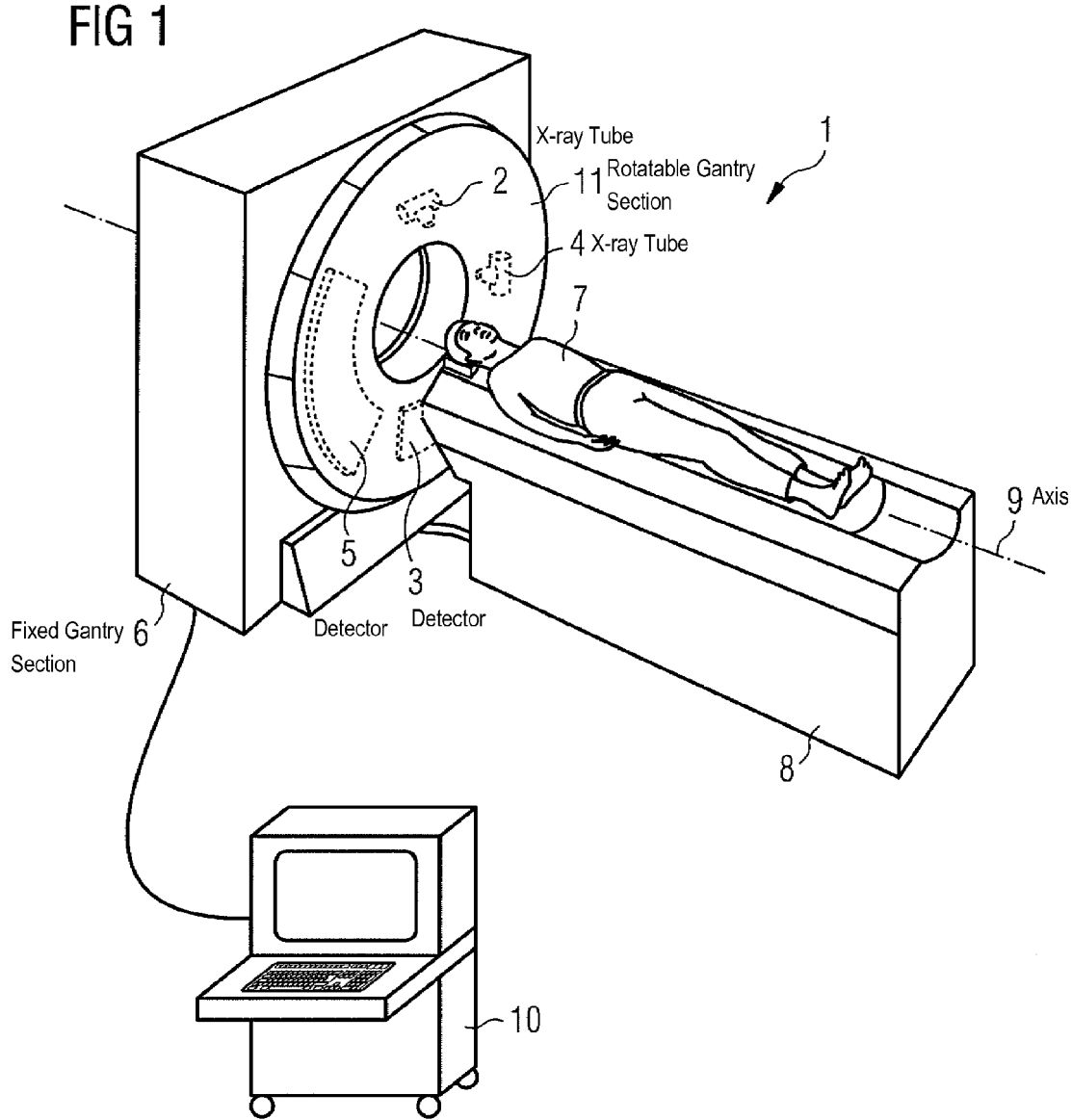
FIG. 1 shows a computed tomography system.

FIG. 1 shows one embodiment of a computed tomography system 1 with a fixed gantry section 6, in which a rotatable gantry section 11 is located. A first tube/detector system is arranged on the rotatable gantry section 11. The tube/detector system includes an X-ray tube 2 and a detector 3. Alternatively, one or a plurality of additional X-ray/detector systems may be attached (e.g., represented optionally with the X-ray tube 4 and an oppositely located detector 5). For investigation purposes, a patient 7 is conveyed into a field of view with the aid of a patient couch 8 that may be slid along an axis 9 of the system, so that an absorption of X-ray radiation may be measured from different projection angles. A computer 10 that is designed as a control and arithmetic unit is employed for control of the system 1. Computer programs that perform control of the system 1, an analysis of measured data, and a reconstruction of desired tomographic image data run on the computer 10.

For example, during transmission of the detector data from the at least one detector on the rotatable gantry section 11, a large mass of data is transmitted via a contactless path. One embodiment of an arrangement for contactless transmission of electrical power and grounding potential is attached to the rotatable gantry section 11 and the fixed gantry section 6 (e.g., two gantry sections), so that signals and the power may be transmitted between the two gantry sections 6, 11 that are rotatable relative to each other. In the FIGS. 2 through 9, exemplary embodiments of the arrangement with a grounding collector are described in greater detail.

Figure 2:
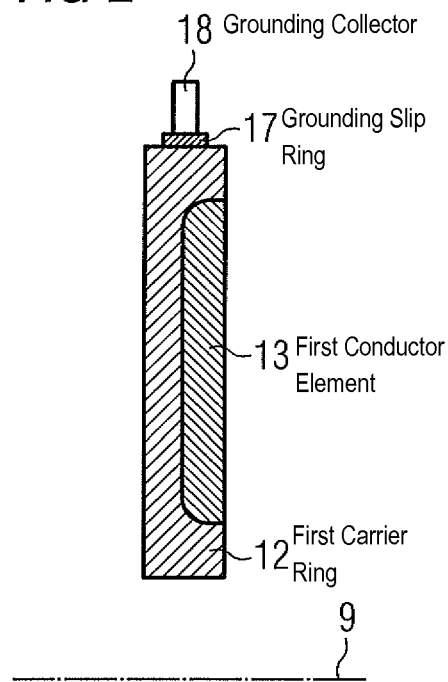
FIG. 2 shows a cross-section through one embodiment of an arrangement including a first carrier ring with a grounding slip ring and a grounding collector.

FIG. 2 shows a cross-section through an annular, electrically conductive first carrier ring 12 (e.g., made of aluminum or steel) that is mounted in a rotationally symmetrical manner on a rotatable gantry section (not shown) of a computed tomography system. A first conductor element 13 in annular form is arranged in the first carrier ring 12 and is electrically insulated from the first carrier ring 12. The first conductor element 13 may receive electrical energy in a contactless manner.

In one embodiment, for the transmission of a system grounding or device grounding, a grounding slip ring 17 is arranged on a cylindrical surface of the first carrier ring 12. The grounding slip ring 17 is connected to the first carrier ring 12 in a conductive manner. A grounding collector 18, which is connected in a conductive manner to a fixed gantry section of the computed tomography system (not shown), slides against the grounding slip ring 17 upon rotation of the first carrier ring 12 about an axis of rotation 9 and thus creates a permanent connection for system grounding. The grounding slip ring 17 includes, for example, a non-abrading metal alloy, and the grounding collector 18 includes, for example, a carbon or a brush.

Figure 3:
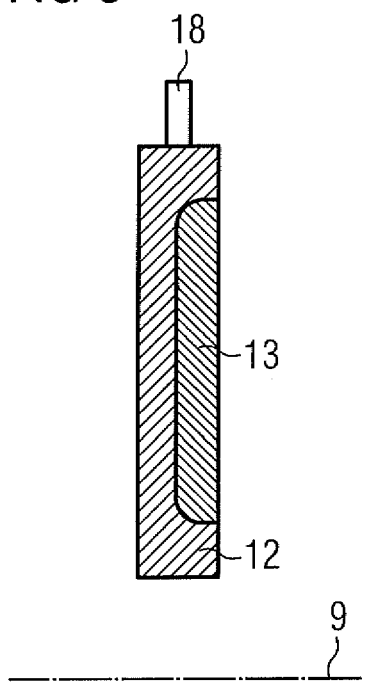
FIG. 3 shows a cross-section through one embodiment of an arrangement including a first carrier ring and a grounding collector.

FIG. 3 shows a cross-section through an annular, electrically conductive first carrier ring 12 (e.g., made of aluminum or steel) that is mounted in a rotationally symmetrical manner on a rotatable gantry section (not shown) of a computed tomography system. A first conductor element 13 in annular form is arranged in the first carrier ring 12 and is electrically insulated from the first carrier ring 12. The first conductor element 13 may receive electrical energy in a contactless manner.

For transmission of a system grounding, a grounding collector 18 that is connected in a conductive manner to a fixed gantry section (not shown) of the computed tomography system is provided. The grounding collector 18 touches the first carrier ring 12 and thus creates a conductive connection between the first carrier ring 12 and the system grounding. Upon a rotation of the first carrier ring 12 about an axis of rotation 9, the grounding collector 18 slides against the cylindrical surface of the first carrier ring 12, and thus creates a permanent connection for system grounding. The grounding collector 18 includes, for example, a brush or carbon.

Figure 4:
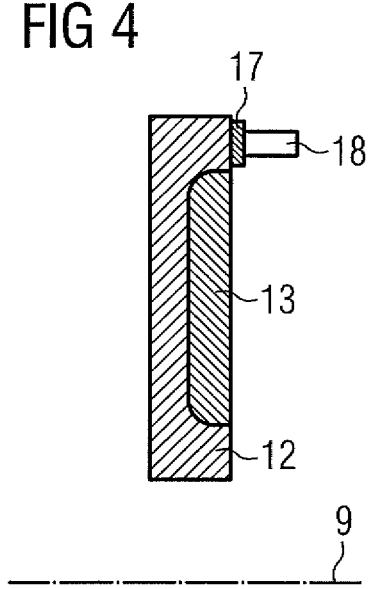
FIG. 4 shows a cross-section through one embodiment of an arrangement including a first carrier ring with a laterally arranged grounding slip ring and a grounding collector.

FIG. 4 shows a cross-section through a first electrically conductive carrier ring 12 in annular form (e.g., made of aluminum or steel) that is mounted in a rotationally symmetrical manner on a rotatable gantry section (not shown) of a computed tomography system. A first conductor element 13 in annular form is arranged in the first carrier ring 12 and is electrically insulated from the first carrier ring 12. The first conductor element 13 may receive electrical energy in a contactless manner.

In one embodiment, for transmission of a system grounding or device grounding, a grounding slip ring 17 is laterally arranged on a face of the first carrier ring 12. The grounding slip ring 17 is connected to the first carrier ring 12 in a conductive manner. A grounding collector 18, which is connected in a conductive manner to a fixed gantry section (not shown) of the computed tomography system, slides against the grounding slip ring 17 upon rotation of the first carrier ring 12 about an axis of rotation 9 and thus creates a permanent connection for system grounding. The grounding slip ring 17 includes, for example, a non-abrading metal alloy, and the grounding collector 18 includes, for example, a carbon or a brush.

Figure 5:
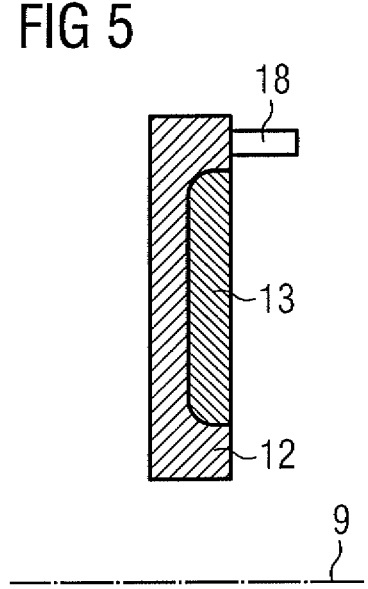
FIG. 5 shows a cross-section through one embodiment of an arrangement including a first carrier ring and a laterally arranged grounding collector.

FIG. 5 shows a cross-section through an electrically conductive first carrier ring 12 in annular form (e.g., made of aluminum or steel) that is mounted in a rotationally symmetrical manner on a rotatable gantry section (not shown) of a computed tomography system. A first conductor element 13 in annular form is arranged in the first carrier ring 12 and is electrically insulated from the first carrier ring 12. The first conductor element 13 may receive electrical energy in a contactless manner.

For transmission of a system grounding, a grounding collector 18 that is connected in a conductive manner to a fixed gantry section (not shown) of the computed tomography system is provided. The grounding collector 18 touches the first carrier ring 12 and thus creates a conductive connection between the first carrier ring 12 and the system grounding. Upon a rotation of the first carrier ring 12 about an axis of rotation 9, the grounding collector 18 slides against a lateral surface of the first carrier ring 12 and thus creates a permanent connection for system grounding. The grounding collector 18 includes, for example, a brush or carbon.

Figure 6:
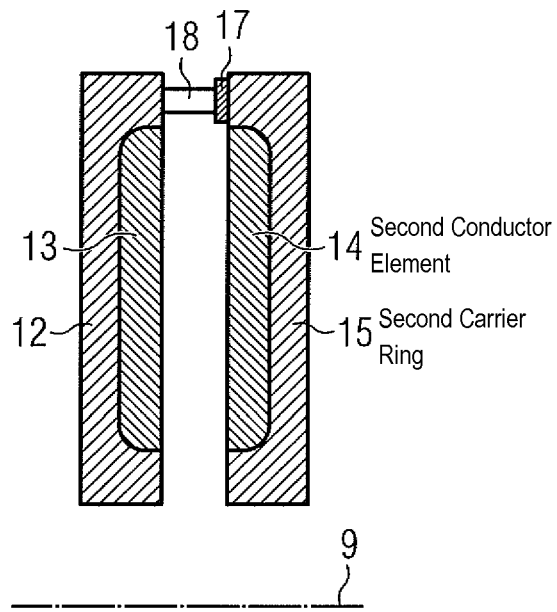
FIG. 6 shows a cross-section through one embodiment of an arrangement including a first carrier ring with a grounding collector and a second carrier ring with a grounding slip ring.

FIG. 6 shows a cross-section through an annular, electrically conductive first carrier ring 12 (e.g., made of aluminum or steel) that is mounted in a rotationally symmetrical manner on a rotatable gantry section (not shown) of a computed tomography system. A first conductor element 13 in annular form is arranged in the first carrier ring 12 and is electrically insulated from the first carrier ring 12. The first conductor element 13 may receive electrical energy in a contactless manner. Also represented is an electrically conductive second carrier ring 15 in annular form arranged parallel to the first carrier ring 12. The second carrier ring 15 is attached to a fixed gantry section (not shown) of the computed tomography system. A second conductor element 14 is arranged in the second carrier ring 15, electrically insulated from the second carrier ring 15. The second conductor element 14 emits electrical power in a contactless manner and transmits the electrical power to the first conductor element 13.

In one embodiment, for transmission of a system grounding or device grounding, a grounding slip ring 17 is arranged on a cylindrical surface of the second carrier ring 15. The grounding slip ring 17 is connected to the second carrier ring 15 in a conductive manner. A grounding collector 18 is connected to the first carrier ring 12 in an electrically conductive manner, such that the grounding collector 18 slides against the grounding slip ring 17 upon rotation of the first carrier ring 12 about an axis of rotation 9 and thus creates a permanent connection for system grounding. The grounding slip ring 17 includes, for example, a non-abrading metal alloy, and the grounding collector 18 includes, for example, a carbon or a brush.

Figure 7:
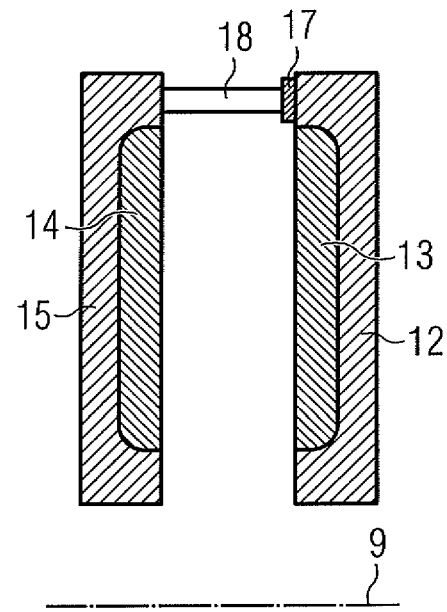
FIG. 7 shows a cross-section through one embodiment of an arrangement including a first carrier ring with a grounding slip ring and a second carrier ring with a grounding collector.

FIG. 7 shows a cross-section through an electrically conductive first carrier ring 12 in annular form (e.g., made of aluminum or steel) that is mounted in a rotationally symmetrical manner on a rotatable gantry section (not shown) of a computed tomography system. A first conductor element 13 in annular form is arranged in the first carrier ring 12 and is electrically insulated from the first carrier ring 12. The first conductor element 13 may receive electrical energy in a contactless manner. Also represented is an electrically conductive second carrier ring 15 in annular form arranged in parallel with the first carrier ring 12. The electrically conductive second carrier ring 15 is attached to a fixed gantry section (not shown) of the computed tomography system. A second conductor element 14 is arranged in the second carrier ring 15 and is electrically insulated from the second carrier ring 15. The second conductor element 14 emits the electrical power in a contactless manner and transmits the electrical power to the first conductor element 13.

In one embodiment, for transmission of a system grounding or device grounding, a grounding slip ring 17 is arranged on a cylindrical surface of the first carrier ring 12. The grounding slip ring 17 is connected to the first carrier ring 12 in an electrically conductive manner. A grounding collector 18 is connected to the second carrier ring 15 in an electrically conductive manner, such that the grounding collector 18 slides against the grounding slip ring 17 upon rotation of the first carrier ring 12 about an axis of rotation 9, and thus creates a permanent connection for system grounding. The grounding slip ring 17 includes, for example, a non-abrading metal alloy, and the grounding collector 18 includes, for example, a carbon or a brush.

Figure 8:
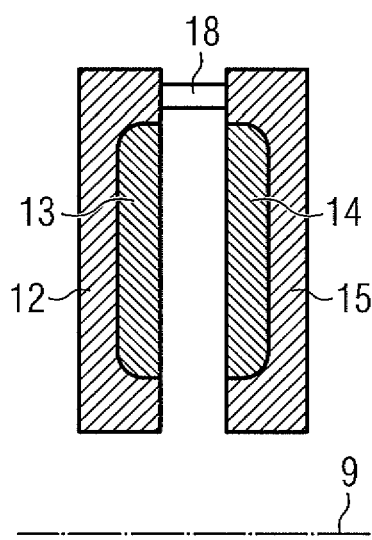
FIG. 8 shows a cross-section through one embodiment of an arrangement including a first carrier ring with a grounding collector and to second carrier ring.

FIG. 8 shows a cross-section through an electrically conductive first carrier ring 12 in annular form (e.g., made of aluminum or steel) that is mounted in a rotationally symmetrical manner on a rotatable gantry section (not shown) of a computed tomography system. A first conductor element 13 in annular form is arranged in the first carrier ring 12 and is electrically insulated from the first carrier ring 12. The first conductor element 13 may receive electrical energy in a contactless manner. Also represented is a second electrically conductive carrier ring 15 in annular form, arranged parallel to the first carrier ring 12. The second electrically conductive carrier ring 15 is attached to a fixed gantry section (not shown) of the computed tomography system. Arranged in the second carrier ring 15 is a second conductor element 14, electrically insulated from the second carrier ring 15. The second carrier ring 15 emits the electrical power in a contactless manner and transmits the electrical power to the first conductor element 13.

For transmission of a system grounding or device grounding, a grounding collector 18 is connected to the first carrier ring 12 in an electrically conductive manner such that upon rotation of the first carrier ring 12 about an axis of rotation 9, the grounding collector 18 slides against the second carrier ring 15 and thus creates a permanent connection for system grounding. The grounding collector 18 includes, for example, a carbon or a brush.

Figure 9:
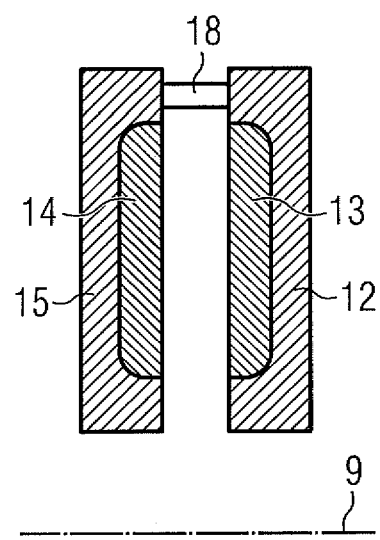
FIG. 9 shows a cross-section through one embodiment of an arrangement including a first carrier ring and a second carrier ring with a grounding slip ring.

FIG. 9 shows a cross-section through an electrically conductive first carrier ring 12 in annular form (e.g., made of aluminum or steel) that is mounted in a rotationally symmetrical manner on a rotatable gantry section (not shown) of a computed tomography system. A first conductor element 13 in annular form is arranged in the first carrier ring 12 and is electrically insulated from the first carrier ring 12. The first conductor element 13 may receive electrical energy in a contactless manner. Also represented is an electrically conductive second carrier ring 15 in annular form arranged in parallel with the first carrier ring 12. The electrically conductive second carrier ring 15 is attached to a fixed gantry section (not shown) of the computed tomography system. A second conductor element 14 electrically insulated from the second carrier ring 15 is arranged in the second carrier ring 15. The second conductor element emits the electrical power in a contactless manner and transmits the electrical power to the first conductor element 13.

For transmission of a system grounding or device grounding, a grounding collector 18 is connected to the second carrier ring 15 in an electrically conductive manner, such that upon rotation of the first carrier ring 12 about an axis of rotation 9, the grounding collector 18 slides against the first carrier ring 12 and thus creates a permanent connection for system grounding. The grounding collector 18 includes, for example, a carbon or a brush.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An arrangement for contactless transmission of electrical power between a fixed gantry section of an X-ray computed tomography system and a gantry section of the X-ray computed tomography system rotatable about an axis of rotation, the arrangement comprising:
a first electrically conductive carrier ring in annular form arranged on the rotatable gantry section;
a second electrically conductive carrier ring in annular form arranged on the fixed gantry section;
at least one first conductor element arranged in or on the first electrically conductive carrier ring, the at least one first conductor element being insulated from the first electrically conductive carrier ring and being for contactless receiving of the electrical power;
at least one second conductor element arranged in or on the second electrically conductive carrier ring, the at least one second conductor element being insulated from the second electrically conductive carrier ring and being for contactless emission of the electrical power; and
at least one grounding slip ring arranged in or on the first electrically conductive carrier ring or the second electrically conductive carrier ring, the at least one grounding slip ring being configured for connecting to the first electrically conductive carrier ring or the second electrically conductive carrier ring in an electrically conductive manner.

2. The arrangement as claimed in claim 1, further comprising at least one grounding collector that is arranged on the second electrically conductive carrier ring.

3. The arrangement as claimed in claim 1, wherein the at least one grounding slip ring is arranged in or on the second electrically conductive carrier ring, the at least one grounding slip ring being connected to the second electrically conductive carrier ring in an electrically conductive manner.

4. The arrangement as claimed in claim 3, further comprising at least one grounding collector that is arranged on the first electrically conductive carrier ring.

5. The arrangement as claimed in claim 3, wherein the at least one first conductor element or the at least one second conductor element is configured in annular form.

6. The arrangement as claimed in claim 1, wherein the at least one grounding slip ring is configured in annular form.

7. The arrangement as claimed in claim 4, wherein the at least one grounding collector forms a sliding contact with the at least one grounding slip ring in an electrically conductive manner.

8. The arrangement as claimed in claim 4, wherein the at least one first conductor element and the at least one second conductor element are configured in annular form.

9. The arrangement as claimed in claim 2, wherein the at least one grounding slip ring is configured in annular form.

10. The arrangement as claimed in claim 3, wherein the at least one grounding slip ring is configured in annular form.

11. The arrangement as claimed in claim 4, wherein the at least one grounding slip ring is configured in annular form.

12. The arrangement as claimed in claim 5, wherein the at least one grounding slip ring is configured in annular form.

13. The arrangement as claimed in claim 1, wherein the at least one grounding slip ring is arranged in or on the first electrically conductive carrier ring, the at least one grounding slip ring being connected to the first electrically conductive carrier ring in an electrically conductive manner.

14. An arrangement for contactless transmission of electrical power between a fixed gantry section of an X-ray computed tomography system and a gantry section of the X-ray computed tomography system rotatable about an axis of rotation, the arrangement comprising:
a first electrically conductive carrier ring in annular form arranged on the rotatable gantry section;
a second electrically conductive carrier ring in annular form arranged on the fixed gantry section;
at least one first conductor element arranged in or on the first electrically conductive carrier ring, the at least one first conductor element being insulated from the first electrically conductive carrier ring and being for contactless receiving of the electrical power;
at least one second conductor element arranged in or on the second electrically conductive carrier ring, the at least one second conductor element being insulated from the second electrically conductive carrier ring and being for contactless emission of the electrical power; and
at least one grounding collector that is arranged on the second electrically conductive carrier ring of the fixed gantry section or the fixed gantry section and forms an electrically conductive sliding contact with the first electrically conductive carrier ring or the rotatable gantry section.

15. An arrangement for contactless transmission of electrical power between a fixed gantry section of an X-ray computed tomography system and a gantry section of the X-ray computed tomography system rotatable about an axis of rotation, the arrangement comprising:
a first electrically conductive carrier ring of the rotatable gantry section;
a second electrically conductive carrier ring in annular form arranged on the fixed gantry section;
at least one first conductor element arranged in or on the first electrically conductive carrier ring, the at least one first conductor element being insulated from the first electrically conductive carrier ring and being for contactless receiving of the electrical power;
at least one second conductor element arranged in or on the second electrically conductive carrier ring, the at least one second conductor element being insulated from the second electrically conductive carrier ring and being for contactless emission of the electrical power; and
at least one grounding collector that is arranged on the first electrically conductive carrier ring, the at least one grounding collector forming an electrically conductive sliding contact with the second electrically conductive carrier ring or the fixed gantry section.

16. An X-ray computed tomography system comprising:
- a gantry comprising a fixed gantry section and a gantry section rotatable about an axis of rotation; and
   - an arrangement for contactless transmission of electrical power between the fixed gantry section and the rotatable gantry section, the arrangement comprising:
   - a first electrically conductive carrier ring in annular form arranged on the rotatable gantry section;
   - a second electrically conductive carrier ring in annular form arranged on the fixed gantry section;
- at least one first conductor element arranged in or on the first electrically conductive carrier ring, the at least one first conductor element being insulated from the first electrically conductive carrier ring and being for contactless receiving of the electrical power;
- at least one second conductor element arranged in or on the second electrically conductive carrier ring, the at least one second conductor element being insulated from the second electrically conductive carrier ring and being for contactless emission of the electrical power; and
- at least one grounding slip ring being arranged in or on the first electrically conductive carrier ring or the second electrically conductive carrier ring, the at least one grounding slip ring being configured for connecting to the first electrically conductive carrier ring or the second electrically conductive carrier ring in an electrically conductive manner.

* * * * *